(12) United States Patent
Trieu et al.

(10) Patent No.: US 8,858,599 B2
(45) Date of Patent: Oct. 14, 2014

(54) SYSTEMS AND METHODS FOR FLEXIBLE SPINAL STABILIZATION

(75) Inventors: Hai H. Trieu, Cordova, TN (US); Michael C. Sherman, Memphis, TN (US); Jeff R. Justis, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1219 days.

(21) Appl. No.: 10/864,181

(22) Filed: Jun. 9, 2004

(65) Prior Publication Data

US 2005/0277922 A1    Dec. 15, 2005

(51) Int. Cl.
*A61F 2/44* (2006.01)
*A61B 17/70* (2006.01)

(52) U.S. Cl.
CPC ......... *A61B 17/7031* (2013.01); *A61B 17/7019* (2013.01); *A61B 17/7004* (2013.01)
USPC ....................................................... 606/257

(58) Field of Classification Search
CPC ........... A61B 17/7031; A61B 17/7002; A61B 17/7019
USPC ........... 623/13.15; 606/61, 63, 254, 255, 259, 606/278, 246, 248, 257, 258, 279; 267/269, 267/270, 281
See application file for complete search history.

(56) References Cited

U.S. PATENT DOCUMENTS

| | | | |
|---|---|---|---|
| 4,697,582 A | 10/1987 | William | |
| 4,708,132 A * | 11/1987 | Silvestrini | ........................ 606/66 |
| 4,743,260 A | 5/1988 | Burton | |
| 5,282,863 A | 2/1994 | Burton | |
| 5,375,823 A | 12/1994 | Navas | |
| 5,415,661 A | 5/1995 | Holmes | |
| 5,425,732 A | 6/1995 | Ulrich | |
| 5,480,401 A | 1/1996 | Navas | |
| 5,540,688 A | 7/1996 | Navas | |
| 5,562,660 A | 10/1996 | Grob | |
| 5,562,736 A * | 10/1996 | Ray et al. | ........................ 606/279 |
| 5,609,634 A * | 3/1997 | Voydeville | ................. 623/13.11 |
| 5,658,286 A | 8/1997 | Sava | |
| 5,672,175 A | 9/1997 | Martin | |
| 5,733,284 A | 3/1998 | Martin | |
| RE36,221 E | 6/1999 | Breard et al. | |
| 6,241,730 B1 | 6/2001 | Alby | |
| 6,267,764 B1 | 7/2001 | Elberg | |
| 6,290,700 B1 | 9/2001 | Schmotzer | |
| 2002/0082598 A1 | 6/2002 | Teitelbaum | |
| 2003/0055427 A1 | 3/2003 | Graf | |
| 2003/0083657 A1 | 5/2003 | Drewry et al. | |
| 2003/0109880 A1 | 6/2003 | Shirado et al. | |
| 2003/0171749 A1 | 9/2003 | Le Couedic et al. | |
| 2003/0191470 A1 | 10/2003 | Ritland | |

(Continued)

FOREIGN PATENT DOCUMENTS

| | | |
|---|---|---|
| EP | 0 669 109 B1 | 2/1994 |
| EP | 0 677 277 A2 | 3/1995 |

(Continued)

*Primary Examiner* — Brian Pellegrino

(57) ABSTRACT

Devices, methods and systems for stabilizing at least a portion of the spinal column are provided. Anchors are engageable to vertebra and a stabilization member is engageable between the anchors. The stabilization member includes an elongate tension member and a compression member in a passage of the tension member.

11 Claims, 6 Drawing Sheets

(56) References Cited

U.S. PATENT DOCUMENTS

| | | |
|---|---|---|
| 2003/0220643 A1 | 11/2003 | Ferree |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0215191 A1* | 10/2004 | Kitchen .......................... 606/61 |
| 2004/0236327 A1* | 11/2004 | Paul et al. ....................... 606/61 |

FOREIGN PATENT DOCUMENTS

| | | | |
|---|---|---|---|
| FR | 2 726 995 A1 | 11/1994 | |
| GB | 2 382 304 | 5/2003 | |
| WO | WO 01/45576 A1 | 6/2001 | |
| WO | WO 03/047442 A1 | 6/2003 | |
| WO | WO 2004016217 A2 * | 2/2004 | ............ A61F 2/44 |
| WO | WO 2004/024011 A1 | 3/2004 | |

* cited by examiner

SYSTEMS AND METHODS FOR FLEXIBLE SPINAL STABILIZATION

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment.

DESCRIPTION OF THE ILLUSTRATED EMBODIMENTS

Figure 1:
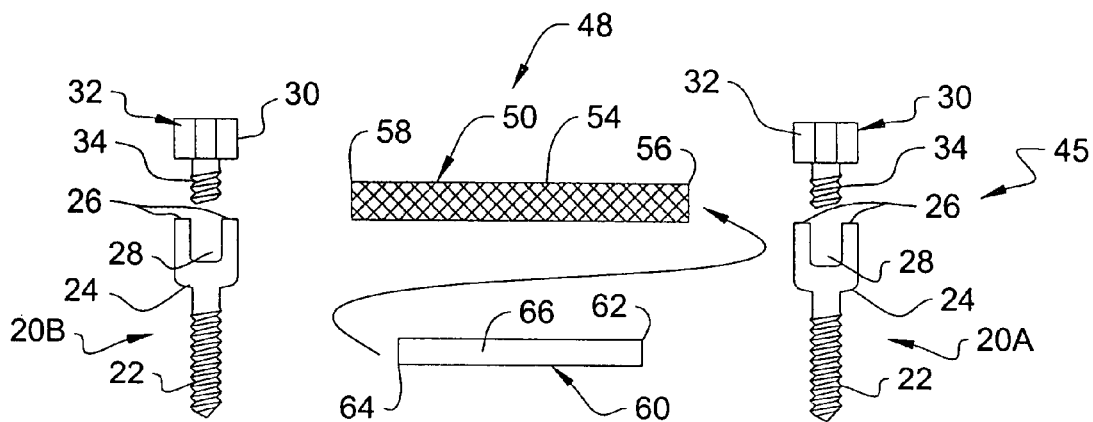
FIG. 1 is an exploded view of a stabilization system.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein are contemplated as would normally occur to one skilled in the art to which the invention relates.

FIG. 1 depicts a spinal stabilization system 45 according to one embodiment for stabilizing at least a portion of the vertebral column. Stabilization system 45 includes a first anchor 20A and a second anchor 20B engageable to bony portions of the spinal column. A stabilization member 48 is positionable between anchors 20A and 20B and engageable to anchors 20A and 20B to provide a stabilization effect to the spinal column.

Stabilization member 48 includes a tension member 50 and at least one compression member 60. Tension member 50 includes a body 54 having a passage 52 extending between opposite ends 56, 58 of body 54. Compression member 60 includes a body 66 extending between ends 62, 64 thereof. Compression member 60 is positionable in passage 52 of tension member 50 to form stabilization member 48. Stabilization system 45 allows at least small degrees of spinal motion in the spinal motion segment to which it is attached since stabilization member 48 is at least partially flexible between adjacent anchors 20A and 20B. When engaged to anchors 20A, 20B, tension member 50 resists movement of the vertebrae away from one another and compression member 60 resists movement of the vertebrae toward one another.

FIG. 1 shows one embodiment of anchor 20 in the form of a uni-axial bone screw. Anchor 20 includes a threaded bone engaging portion 22 and a receiver member 24. Receiver member 24 includes a passage 28 for receiving stabilization member 48 between arms 26 of receiver member 24. A plug 30 is attachable to receiver member 24 to secure stabilization member 48 relative to anchor 20. In the illustrated embodiment, plug 30 includes a set screw portion 34 engageable to internal threads provided along arms 26, and a head portion 32 engageable by a driving tool.

Other embodiments contemplate other forms for anchor 20. For example, the bone engaging portion can be a hook, staple, rivet, expansion anchor, or other suitable device for engaging bony structure. The receiver member can be U-shaped for top-loading of the stabilization member 48 as shown. Other embodiments include side-loading or bottom loading receiver members. The receiver member can include any suitable form for engagement with stabilization member 48. Receiver member 24 can also be rotatably mounted on bone engaging portion 22 to provide multi-axial capabilities. Plug 30 can be configured for engagement around receiver member 24. Plug 30 can be engaged with receiver member 24 by means other than threaded engagement, including interference fits, snap fits or bayonet locks, or auxiliary fixation elements such as sutures, pins, or adhesives, for example.

Stabilization system 45 can be employed in the treatment of various spinal conditions, such as spinal stenosis, scoliosis, degenerative disc disease, disc herniation, and vertebral fractures, for example. Stabilization system 45 can also be employed in combination with various treatment systems, including providing supplemental instrumentation for procedures that include the placement of spinal fusion devices, artificial disc devices, nucleus replacement devices, and procedures which remove disc and bone material, such as discectomy procedures, nucleotomy procedures, laminectomy procedures, and facectomy procedures, for example. Stabilization system 45 provides compression load sharing and intervertebral space distraction at the treated spinal levels while allowing limited motion of the spinal motion segments due to the flexibility of the tension member and compression member components of the system. For example, depending on the attachment location of system 45, excessive load on degenerated disc and facet joints can be reduced or eliminated through the compression load sharing capabilities provided by compression member 60. The disc space and facet joints can also be distracted with compression member 60 maintaining the distraction to provide a desired spacing between the bone on opposite sides of the effected joints.

Stabilization system 45 may include a single or multi-level composite stabilization member 48 and anchors to engage the stabilization member to two or more vertebrae. In one embodiment, stabilization member 48 includes tension member 50 in the form of a flexible outer sheath that resists tension when engaged to the anchors, and compression member 60 is housed within the outer sheath to resist compression between the anchors when tension member 50 is engaged to the anchors. Stabilization member 48 can be anchored to posterior elements of the vertebrae of the spinal column using anchors 20A, 20B or any other suitable anchoring device. Stabilization member 48 can also be secured along the anterior portions of the vertebrae of the spinal column using anchors 20A, 20B or any other suitable anchors. Multiple stabilization members 48 can be secured along the same one or same multiple vertebral levels. It is also contemplated that multiple stabilization members 48 can be secured along different vertebral levels along the spinal column. The same stabilization member 48 can also be adapted to extend along multiple vertebral levels of the spinal column.

When stabilization system 45 is engaged to the spinal column, the treated levels of the spinal column are partially unloaded by compression member 60. Excessive extension of the vertebral level or levels is resisted by compression member 60, and excessive flexion of the treated vertebral level or levels is resisted by the flexible outer sheath of tension member 50. The tension and compression members 50, 60 act together to resist excessive lateral bending and axial rotation of the one or more vertebral levels that are being treated.

Figure 2:
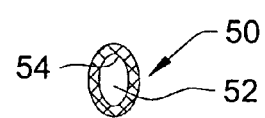
FIG. 2 is an end view of a tension member of the stabilization system of FIG. 1.
Figure 4:
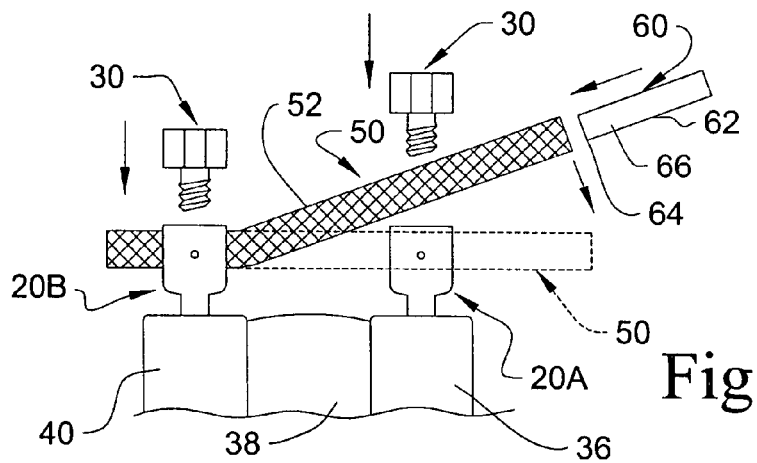
FIG. 4 is an elevation view showing attachment of the stabilization system to vertebrae of the spinal column.

In FIG. 4 there is shown a first vertebra 36 and a second vertebra 40 positioned on opposite sides of a disc space 38. First anchor 20A is engaged to first vertebra 36, and second anchor 20B is engaged to second vertebra 40. With compression member 60 removed, tension member 50 includes a collapsible structure as shown in FIG. 2. Second end 58 of tension member 50 is positioned in the receiver member of second anchor 20B. Plug 30 is engaged to second anchor 20B to secure second end 58 therein. Since tension member 50 is collapsible, second end 58 is crimped between the lower surface of receiver 24 and plug 30 when secured in anchor 20B.

Figure 3:
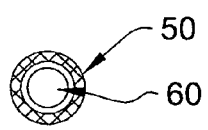
FIG. 3 is an end view of the tension member of FIG. 2 with a compression member in a passage thereof to form a stabilization member.

Compression member 60 can then be loaded through the opening of tension member 50 adjacent first end 56. Compression member 60 occupies passage 52 so that tension member 50 conforms to the outer shape of compression member 60, as shown in FIG. 3. Compression member 60 has a length between ends 62, 64 sized to extend between and abut the sides of anchors 20A and 20B oriented toward one another, and as seen in FIGS. 1 and 3-6 among others, compression member 60 may have a constant diameter over the entirety of that length prior to loading into tension member 50 or in other uncompressed states. In one embodiment, compression member 60 can be compressed between its outer ends and positioned between anchors 20A, 20B and then released to expand against anchors 20A, 20B to distract the space between anchors 20A, 20B.

Tension member 50 is positioned in passage 28 of receiver 24 of first anchor 20A and secured therein. Plug 30 of first anchor 20A is engaged thereto to crimp or collapse tension member 50 between the bottom surface of first anchor 20A and plug 30. Compression member 60 extends between and abuts the anchors 20A, 20B to function as a shock absorber while allowing limited movement of anchors 20A, 20B toward one another upon movement of vertebrae 36, 40. If necessary or desirable, the portion of tension member 50 extending through first anchor 20A away from second anchor 20B can then be severed to minimize the length of the tension member 50 extending from first anchor 20A.

Figure 6:
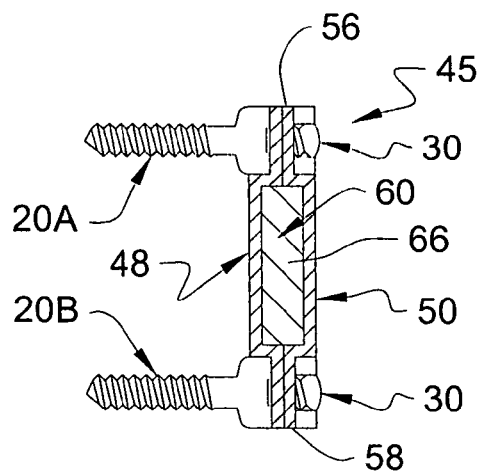
FIG. 6 is a section view of the stabilization system.

As shown in FIG. 6, when tension member 50 is engaged to anchors 20A, 20B, first and second ends 56, 58 are crimped in the respective anchor 20A, 20B between bottom surfaces of the receiver members and the plug engaged to the anchor. The crimping of ends 56, 58 collapses passage 52 of tension member 50 in receiver 24 of anchors 20A, 20B. The flexibility of tension member 50 allows passage 52 to be contoured from this crimped configuration to a shape that is restored upon positioning of compression member 60 in passage 52.

Figure 5:
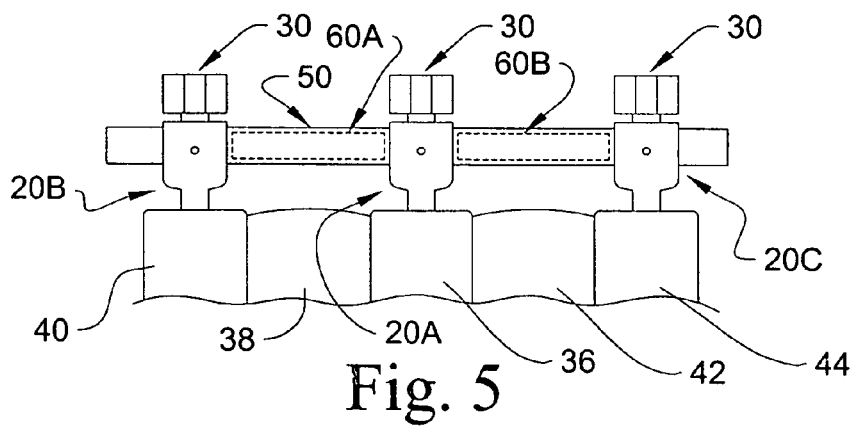
FIG. 5 is an elevation view showing the stabilization system attached to multiple vertebral levels.

In a further embodiment, a third anchor 20C can be engaged to a third vertebra 44 on the other side of disc space 42, as shown in FIG. 5. A second compression member 60B is positioned in the portion of passage 52 of tension member 50 extending from first anchor 20A. The end of tension member 50 is positioned in passage 28 of third anchor 20C and secured therein with a plug. Second compression member 60B extends between anchors 20A and 20C, and functions as a shock absorber to resist movement of anchors 20A, 20C and thus vertebrae 36, 44 toward one another.

Figure 7:
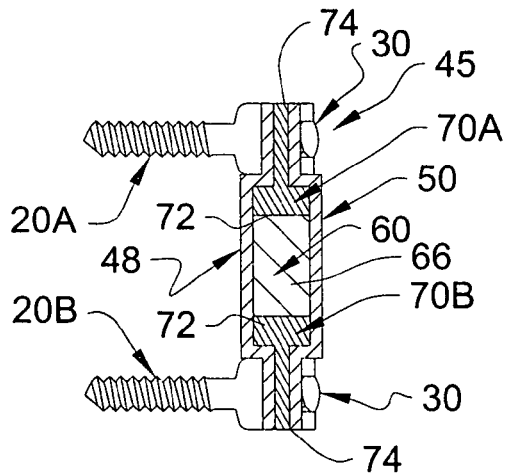
FIG. 7 is a section view of another embodiment stabilization system.

In FIG. 7, stabilization system 45 includes stabilization member 48 engaged to first and second anchors 20A and 20B. Stabilization member 48 includes a compression member 60 having rigid portions 70A, 70B at opposite ends of an intermediate compressible body 66. Rigid portions 70A, 70B provide a more rigid interface between tension member 50 and the respective anchor 20A, 20B than is provided by engaging tension member 50 between the anchor and plug as shown in FIG. 6. Rigid portion 70A includes an enlarged end portion 72 positionable adjacent the respective end of intermediate compressible body 66, and a stem 74 extending from end portion 72 and through the receiver member 24 of the respective anchor 20A, 20B. In the illustrated embodiment, rigid portions 70A, 70B are T-shaped. Other shapes are also contemplated, including funnel shapes and mushroom shapes for example.

Plugs 30 are engageable to the respective anchor 20A, 20B to clamp the stem 74 between the plug and the anchor seat. Rigid portions 70A, 70B can be more rigid than compressible body 66, providing a rigid platform extending from anchors 20A, 20B against which the ends of the intermediate compressible body 66 bear in resisting compression loading. The rigid stem 74 may also provide greater resistance to slippage of tension member 50 in anchors 20A, 20B since tension member 50 is not collapsed upon itself, but rather engages stem 74 when engaged in anchors 20A, 20B. End portions 72 are enlarged and sized to mate with the ends of the intermediate compressible body 66 of compression member 60 to distribute the compression load thereto.

Figure 8:
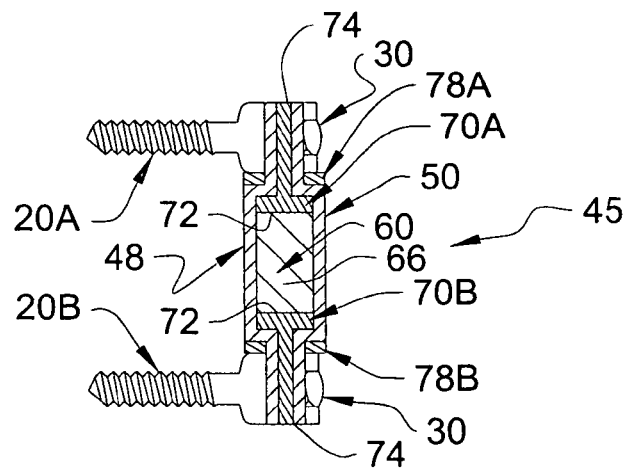
FIG. 8 is a section view of another embodiment stabilization system.

In FIG. 8 stabilization system 45 includes washers 78A, 78B at opposite ends of tension member 50 adjacent the respective anchor 20A, 20B. Washers 78A, 78B include a central aperture extending therethrough through which tension member 50 and the respective stem 74 of rigid portions 70A, 70B are received. Washers 78A, 78B abut the respective adjacent end portion 72 of rigid portion 70A, 70B, with tension member 50 extending therebetween. Washers 78A, 78B provide a platform against which the adjacent receiver 24 of anchors 20A, 20*b* can be positioned to distribute compression loading through the adjacent rigid portion 70A, 70B to compression member 60.

In another embodiment, washers 78A, 78B are employed in system 45 without rigid portions 70A, 70B. In this embodiment, washers 78A, 78B abut the ends of body 66 of compression member 60 with tension member 50 extending therebetween. In another embodiment, multiple washers are employed at one or both ends of tension member 50 to occupy the space between the adjacent receiver 24 of anchors 20A, 20B and either the compression member 60 or rigid portion 70A, 70B. In this embodiment, the washers allow the compression member to positioned in contact with the anchors 20A, 20B through the washers 78 even through the length of compression member 60 may not be sufficient to extend the entire distance between the anchors.

Figure 9:
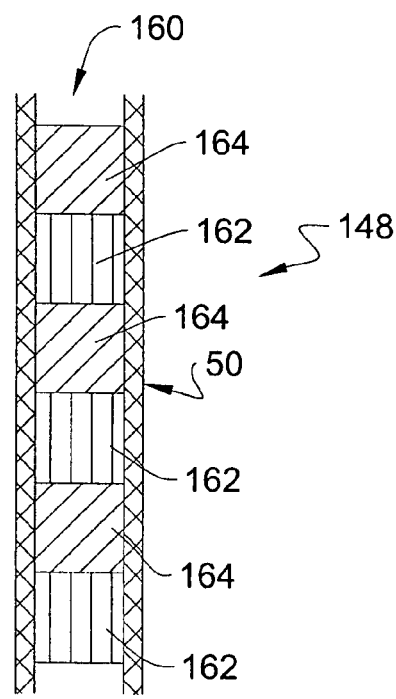
FIG. 9 is a section view of another embodiment stabilization member.
Figure 10:
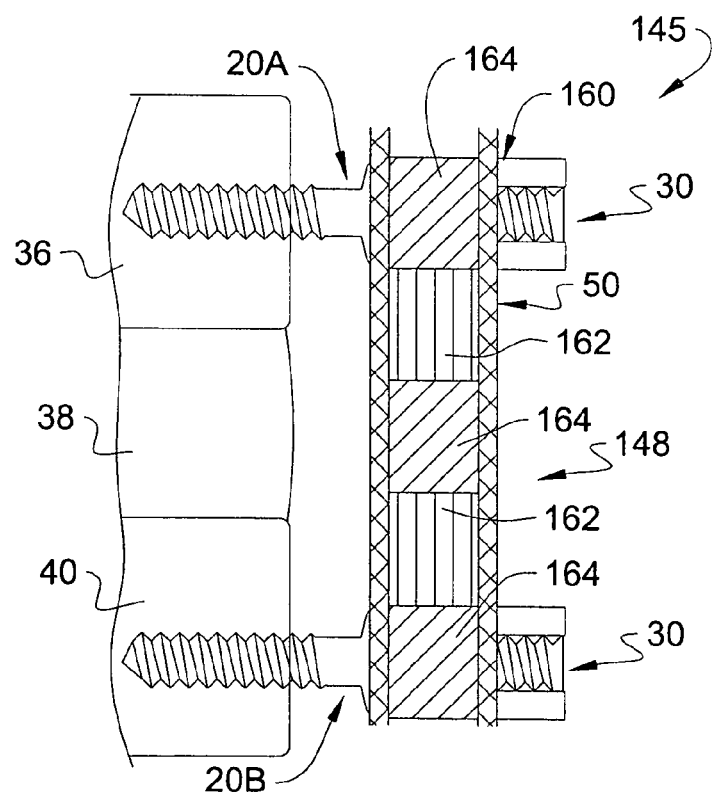
FIG. 10 is a section view showing the stabilization member of FIG. 9 engaged to vertebrae of a spinal column.

FIG. 9 shows another embodiment stabilization member 148 which includes tension member 50 and a compression member 160. Compression member 160 includes a plurality of alternately positioned rigid portions 164 and compressible portions 162. As shown in FIG. 10, stabilization member 148 is engaged to vertebrae 36, 40 with anchors 20A, 20B. The rigid portions 164 are aligned with the receivers 24 of the anchors 20A, 20B and engaged thereto with the plug. One or more intermediate rigid portions 164 are positioned between compressible portions 162.

Figure 11:
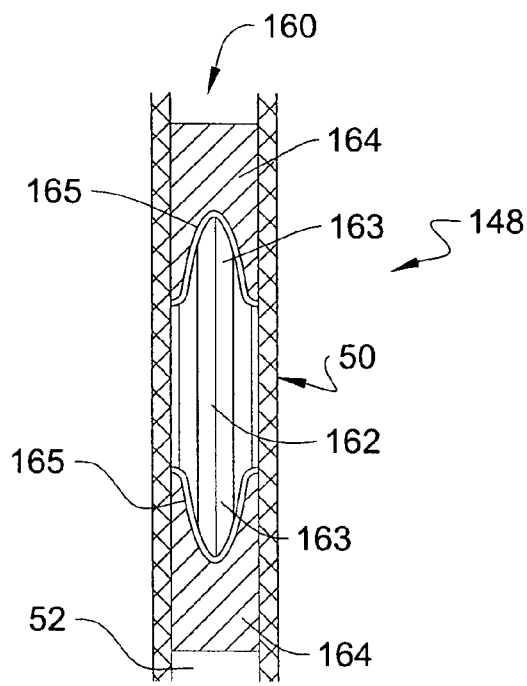
FIG. 11 is a section view of another embodiment stabilization member.

In FIG. 9 compressible portions 162 and rigid portions 164 are cylindrical in shape and are positioned in tension member 50 to abut one another in end-to-end fashion. Other shapes for alternating rigid and compressible portions are also contemplated. For example, in FIG. 11 rigid portions 164 each include a receptacle 165 oriented toward the other rigid portion 164. Compressible portion 162 includes opposite extensions 163 that are received in adjacent ones of the receptacles 165. In the illustrated embodiment, the receptacles 165 are concavely curved and the extensions 163 are convexly curved to eliminate sharp and abrupt corners in the interface between extensions 163 and receptacles 165. The concave-convex interface provides stability to compression member 160 to resist lateral or axial slipping of the portions of the compression member 160 relative to one another. Other axial interfaces are also contemplated, including telescoping components and other interdigitating arrangements between the rigid and compressible portions. In another embodiment, an elongated member, such as a suture or strand, extends through aligned central apertures of portions 162, 164. The elongated member is engaged at opposite ends of compression member 160 to maintain the adjacent rigid and compressible portions in alignment with one another and in axial position relative to one another.

Figure 12:
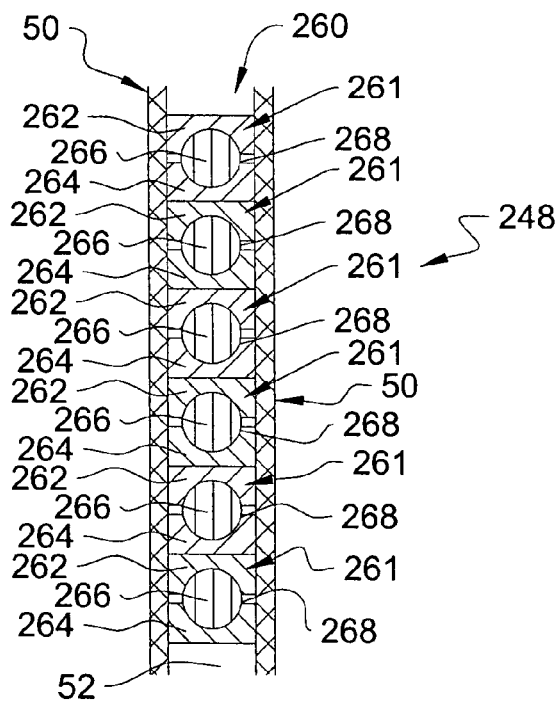
FIG. 12 is a section view of another embodiment stabilization member.

Referring to FIG. 12, there is shown another embodiment compression member 260 positioned in passage 52 of tension member 50. Compression member 260 includes a number of compression elements 261 that each includes a central compressible portion 266. Compression elements 261 further include upper and lower rigid portions 262 positioned on opposite sides of compressible portion 266. Rigid portions 262, 264 are separated by a gap 268 which allows rigid portions 262, 264 to moved toward one another in response to compression of compressible portion 266. A series of compression elements 261 can be placed one adjacent the other along passage 52 with the adjacent rigid portions abutting one another in end-to-end fashion.

In the illustrated embodiment, rigid portions 262, 264 include concavely curved recesses oriented toward one another that receive compressible portion 266 therebetween. Rigid portions 262, 264 extend axially along at least a portion of compressible portion 266 to laterally and axially constrain compressible portion 266 therebetween. Compressible portion 266 includes a rounded or spherical shape to provided a uniform transition of compressive forces between adjacent ones of the compression elements 261.

Figure 13:
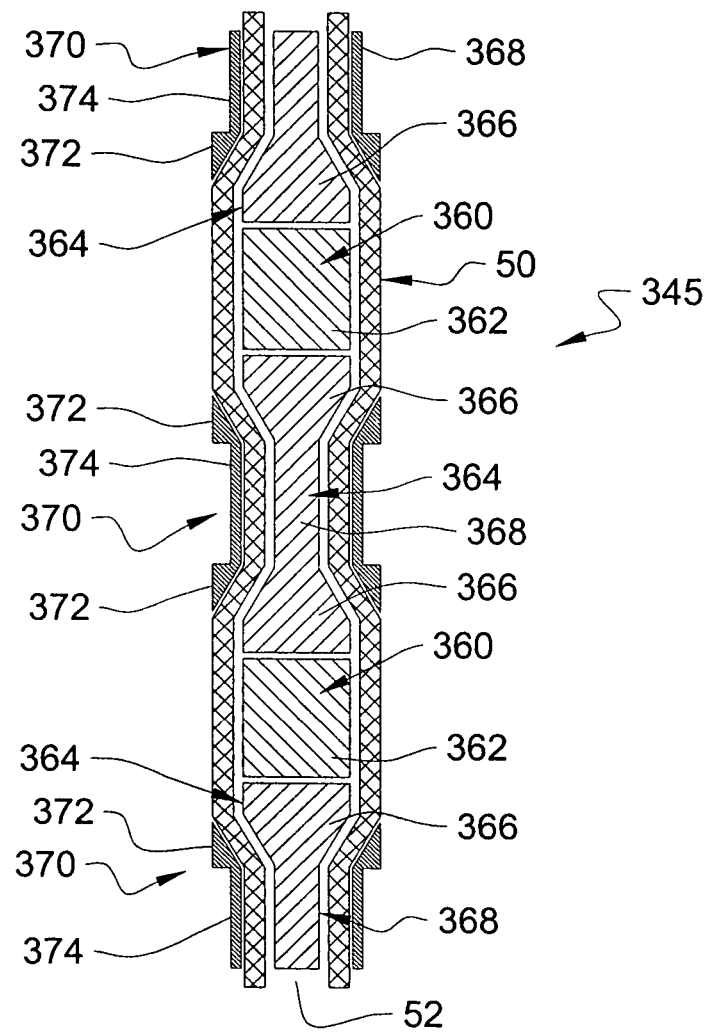
FIG. 13 is a section view of another embodiment stabilization member.

Referring now to FIG. 13, there is shown another embodiment stabilization member 345 which includes tension member 50 and compression member 360 in passage 52 of tension member 50. Compression member 360 includes a compressible portion 362 and rigid portions 364. The intermediate rigid portion 364 includes a dumbbell type shape with enlarged end portions 366 and a stem 368 extending between enlarged end portions 366. Rigid portions 364 contact the adjacent end of an adjacent compressible portion 362. In the illustrated embodiment, the rigid portions 364 at the ends of compression member 360 include only a single enlarged end portion 366, and a stem 368 extending therefrom to a free end.

Stabilization member 345 further includes a rigid sleeve 370 positioned about stem 368 and tension member 50 along the intermediate rigid portion 364. Sleeve 370 includes opposite enlarged ends 372 and a sleeve portion 374 extending between ends 372. Enlarged ends 372 extend radially outwardly about sleeve portion 374, and contact an adjacent one of end portions 366 of rigid portion 354 with tension member 50 extending therebetween. At the opposite ends of compression member 360, there are provided rigid sleeves 370 that include only a single enlarged end 372 at one end of a rigid sleeve portion 374.

The rigid sleeves 370 provide fixation locations along stabilization member 345 for engagement of anchors 20A, 20B to stabilization member 345. Sleeves 370 are positioned with sleeve portion 374 in passage 28 of the respective anchor with enlarged ends 372 in contact with arms 26 of the anchor. Enlarged ends 372 axially constrain sleeve 370 in the respective anchor. Enlarged ends 372 also abut enlarged end portions 366 with tension member 50 therebetween to axially constrain compression member 360 between the anchors. Furthermore, sleeve portions 374 of sleeves 370 provide a barrier between tension member 50 and the plug and anchor to protect tension member 50 from cutting or tearing upon engagement of the plug with the anchor.

Figure 14:
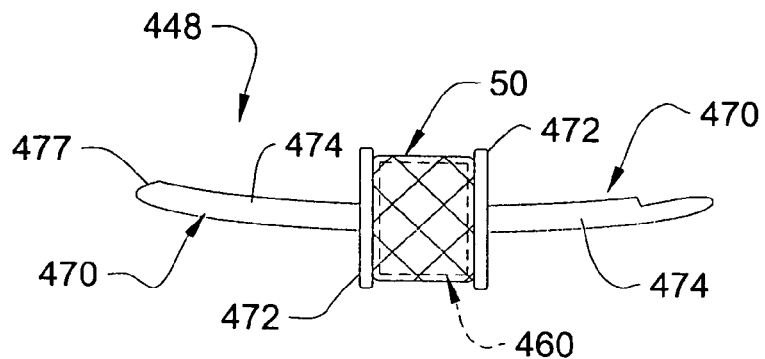
FIG. 14 is an elevation view of another embodiment stabilization member.
Figure 15:
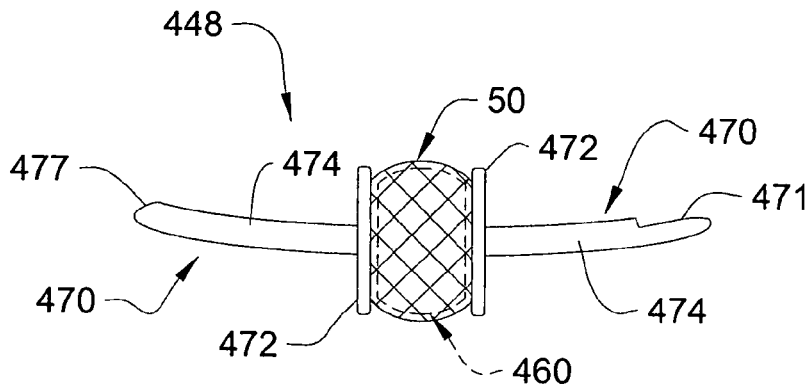
FIG. 15 is an elevation view of the stabilization member of FIG. 14 subjected to a compression load.
Figure 16:
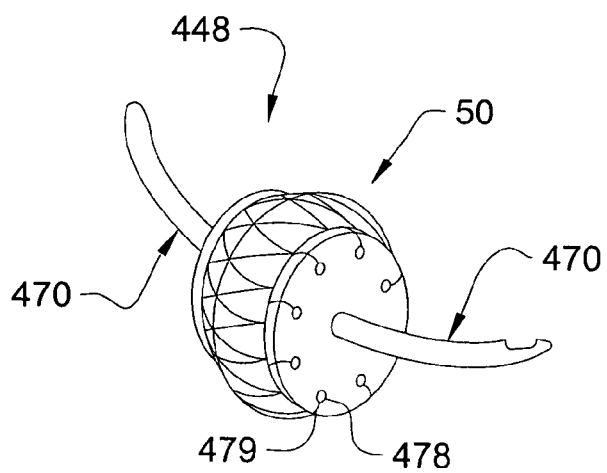
FIG. 16 is a perspective view of the stabilization member of FIG. 15.

Referring to FIGS. 14-16, another embodiment stabilization member 448 is shown. Stabilization member 448 includes an intermediate portion having a tension member 50 and a compression member 460 positioned in tension member 50. Tension member 50 is comprised of a flexible outer sleeve having a passage for receiving compression member 460. Rigid portions 470 are engaged to and extend from opposite ends of tension member 50 and compression member 460. Rigid portions 470 include an enlarged end portion 472 adjacent to and in abutting engagement with the ends of tension member 50 and compression member 460. A stem 474 extends from enlarged end portion 472 and away from tension member 50 and compression member 460. Stem 474 is positionable in the passage of a receiver of an anchor, and engageable in the anchor with plug to secure stabilization member to respective ones of adjacent vertebrae.

Tension member 50 is flexible and restrains movement of the anchors away from one another. Movement of the anchors toward one another is restrained by compression member 460, which can bulge outwardly in tension member 50 when a compression load is applied to the ends thereof through rigid portions 470, as shown in FIGS. 15 and 16. Accordingly, stabilization member 448 allows limited motion of the spinal motion segment while providing flexible restraint in flexion, extension and rotation. As the intermediate portion is subjected to loading of the spinal column, rigid portions 470 are moveable relative to one another in response to tensioning of compression of tension member 50 and/or compression member 460.

Various modes of attachment of rigid portions 470 with tension member 50 and/or compression member 460 are contemplated. In the illustrated embodiment, enlarged end portions 472 include a plurality of holes 478 that receive threads 479 extending through tension member 50 and/or compression member 460. Other embodiments contemplate rigid portions 470 are attached by fasteners, molding, fusing, gluing or otherwise securing rigid portions to tension member 50 and/or compression member 460.

In one embodiment, stabilization member 448 is adapted for engagement with a percutaneous insertion instrument, such as is disclosed in U.S. Pat. No. 6,530,929 and U.S. patent application Ser. No. 10/769,569, each of which is incorporated herein by reference. One of the rigid portions 470 includes a tapered leading end 477 to facilitate percutaneous placement, and the other rigid portion 470 includes a recess 471 to facilitate engagement with the insertion instrument in a predetermined orientation.

Tension member 50 can be made from any suitable material, including polymers, metals, or ceramics, for example. Examples of suitable polymers include elastomers, plastics, rubber and any polymer capable of being processed into high performance synthetic fibers. Examples of suitable synthetic fibers include polyethylene, polyesters, polyvinyl alcohol, polyaryletherketone, polyurethane, copolymer of silicone and polyurethane. Tension member 50 can be made from any copolymer, blend, composite or laminate of synthetic fiber material. Examples of copolymers suitable for synthetic fiber material include silicone-polyurethane copolymers. Examples of blends for synthetic fiber material include silicone with polyurethane. Examples of composites of synthetic fiber material include polyester mesh or fiber within polyurethane. Examples of laminates for synthetic fiber material include braided polyester tubing and silicone polyurethane copolymers. In one embodiment, tension member 50 is formed by braided synthetic fibers woven into a tube.

Tension member 50 can be provided in any length ranging from 0.5 cm or less to 100 cm or more. In one embodiment, the length is sized to extend through adjacent anchors engaged to vertebrae on each side of a vertebral level. Tension member 50 can include any cross-sectional shape, including round, oval, rectangular, square, hexagonal or any other suitable shape for receiving the compression member therein. Tension member 50 can be made by braiding, weaving, knitting, sewing, extrusion, injection molding, compression molding, casting, bonding or laminating, for example.

The compression members can be made from any suitable material, including polymers, metals, or ceramics. Examples of suitable polymers include elastomers, plastics and rubber. Examples of suitable elastic or rubbery polymers include silicone, polyurethane, copolymer of silicone and polyurethane, polyolefin, and hydrogels. The compression members can be made from any copolymer, blend, composite or laminate of the polymer materials. Examples of copolymers include silicone-polyurethane copolymers. Examples of blends include silicone with polyurethane. Examples of composites include polyester mesh or fiber within polyurethane. Examples of laminates include multiple layers of polyester mesh and silicone polyurethane copolymers.

The compression members can be provided in any length ranging from 0.5 cm and less to 100 cm or more. In one embodiment, the length is sized to extend between adjacent anchors engaged to vertebrae on each side of a vertebral level. In another embodiment, the compression member is provided with compressible portions and rigid portions and/or washers as discussed above that allow the length of the compression member to be adjusted by adding or removing the compressible portions, rigid portions, and/or washers from compression member 60. The compression member can include any cross-sectional shape, including round, oval, rectangular, square, hexagonal or any other suitable shape. The diameter or width of the compression member may be constant over its whole length when it is in an uncompressed state. The surfaces of the compression member can include features on or under the surface that provide a desired modification to material behavior. Such features include grooves, holes, voids, cavities, extensions, receptacles, or other features that can modify stiffness, compliance, shock absorption, compression resistance, and/or engagement with an adjacent rigid portion, for example. The compression members can be made by any suitable process, including extrusion, injection molding, compression molding, casting, bonding, laminating or machining, for example.

In the illustrated embodiments, the compression members are removably received in tension member 50. It is also contemplated that tension member 50 and the compression member positioned therein can be physically bonded to one another. Tension member 50 can be molded in attachment with the compression member to form a unitary composite structure. The compression member can be comprised of one or more compressible portions alone or in combination with one or more rigid portions. The compressible and rigid portions can be separate components, can be formed as an integral member, or can be fastened to one another with adhesives, fusion or fasteners.

It is also contemplated that compression member can by provided with multiple sections having differing levels of stiffness or other physical characteristic to work in concert with one another in the stabilization system. Tension member 50 can be fastened to rigid portions of the compression member in the anchors. Alternatively, a rigid sleeve can be placed about tension member 50 with a rigid portion of the compression member extending through the outer sleeve as well. The rigid outer sleeve provides an attachment location along the stabilization member for engagement to the bone anchors.

It should be understood that the stabilization systems discussed herein may be utilized in all regions of the spine, including the cervical, thoracic, lumbar, lumbo-sacral and sacral regions of the spine. It should also be understood that the stabilization systems may extend across a spinal motion segment having only two vertebrae or more than two vertebrae. It is further contemplated two or more stabilization systems may be employed simultaneously along the same spinal motion segment. Additionally, although the stabilization systems are suited for applications in a posterior region of the spinal motion segment or segments, the stabilization system may alternatively or additionally be applied in other surgical approaches and combinations of surgical approaches to the spinal motion segment, including anterior, antero-lateral, lateral, and/or postero-lateral portions of the spinal motion segment or segments.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A spinal stabilization system for providing stabilization between a first vertebra and a second vertebra comprising:

a first anchor configured to engage with the first vertebra, wherein the first anchor includes a first receiver member of which includes a first receiver passage through the first receiver member;

a second anchor configured to engage with the second vertebra, wherein the second anchor includes a second receiver member of which includes a second receiver passage through the second receiver member;

a tension member including a body and a passage through the body that extends between a first end of the tension member and a second end of the tension member that is opposite from first end of the tension member, wherein the tension member is coupled within the first receiver member near the first end and is coupled within the second receiver member near the second end, a compression member including first and second ends positioned within the passage through the body of the tension member, and the compression member is not received within the first receiver passage of the first receiver member or configured to extend the distance between the first and second anchor such that the second receiver member when the tension member is coupled to the first receiver member and the second receiver member wherein the first and second ends of the tension member are crimped to collapse the passage when coupled within the first and second receiver passages respectively, and wherein the tension member with the compression member positioned therein are configured to resist movement of the first vertebra and the second vertebra away from and toward one another respectively by abutting both the first anchor and the second anchor resulting from the compression member extending the distance between the anchors from within a portion of the tension member.

2. The spinal stabilization system of claim 1 wherein the tension member is a tubular shape made by one or more of braiding, weaving, knitting, sewing, extrusion, injection molding, compression molding, casting, bonding, and laminating.

3. The spinal stabilization system of claim 1 wherein the tension member comprises one or more of polymers such as elastomers, plastics, and rubber, synthetic fibers such as polyethylene, polyesters, polyvinyl alcohol, polyaryletherketone, polyetheretherketone, polyurethane, and copolymer of silicone and polyurethane, metals, and ceramics.

4. The spinal stabilization system of claim 1 wherein the compression member has a length that extends between its first end and its second end and has a substantially uniform width along its length.

5. The spinal stabilization system of claim 1 wherein the compression member is positioned within the passage through the body of the tension member such that the compression member is not attached to the tension member by tensile forces between the compression member and the tension member.

6. The spinal stabilization system of claim 1 wherein the compression member is an elastomer that comprises one or more of silicone, polyurethane, polyolefin, and hydrogel.

7. A spinal stabilization system for providing stabilization between a first vertebra and a second vertebra comprising:

a first anchor configured to engage with the first vertebra, wherein the first anchor includes a first receiver member, and the first receiver member includes a first receiver passage through the first receiver member;

a second anchor configured to engage with the second vertebra, wherein the second anchor includes a second receiver member, and the second receiver member includes a second receiver passage through the second receiver member;

a tension member including a body and a passage through the body that extends between a first end of the tension member and a second end of the tension member that is opposite from first end of the tension member, wherein the tension member is coupled within the first receiver passage near the first end of the tension member such that the tension member is crimped to collapse the passage through the body of the tension member, and wherein the tension member is coupled within the second receiver passage near the second end of the tension member such that the tension member is crimped to collapse the passage through the body of the tension member; and a compression member having a length that extends between its first end and its second end and has a substantially uniform width along its length is positioned within the passage through the body of the tension member such that the length the compression member between the first end and the second end extends between the anchors, and the compression member is not received within the first receiver passage or the second receiver passage, and wherein the tnesion member with the compression member positioned therein are configured to resist movement of the first vertebra and the second vertebra away from and toward one another respectively by abutting both the first anchor and the second anchor from within a portion of the tension member.

8. The spinal stabilization system of claim 7 wherein the tension member is a tubular shape made by one or more of braiding, weaving, knitting, sewing, extrusion, injection molding, compression molding, casting, bonding, and laminating.

9. The spinal stabilization system of claim 7 wherein the tension member comprises one or more of polymers such as elastomers, plastics, and rubber, synthetic fibers such as polyethylene, polyesters, polyvinyl alcohol, polyaryletherketone, polyetheretherketone, polyurethane, and copolymer of silicone and polyurethane, metals, and ceramics.

10. The spinal stabilization system of claim 7 wherein the compression member is positioned within the passage through the body of the tension member such that the compression member is not attached to the tension member by tensile forces between the compression member and the tension member.

11. The spinal stabilization system of claim 7 wherein the compression member is an elastomer that comprises one or more of silicone, polyurethane, polyolefin, and hydrogel.

* * * * *